United States Patent [19]
Omachi

[11] Patent Number: 5,454,374
[45] Date of Patent: Oct. 3, 1995

[54] PRESSURE-MEASURING METHOD AND NEEDLE SYSTEM FOR HEMODIALYSIS

[76] Inventor: Rodney S. Omachi, 345 San Fernando Way, San Francisco, Calif. 94127

[21] Appl. No.: 822,416

[22] Filed: Jan. 17, 1992

[51] Int. Cl.⁶ .................................................. A61B 5/00
[52] U.S. Cl. ........................... 128/673; 128/674; 128/675; 73/708
[58] Field of Search ............................ 73/708, 714, 756; 116/DIG. 47, 281, 283, 341; 128/674, 673, 675, 684

[56] References Cited

U.S. PATENT DOCUMENTS

| | | | |
|---|---|---|---|
| 3,062,202 | 11/1962 | Hyman et al. | 128/2.05 |
| 3,610,230 | 10/1971 | Anderson | 128/674 |
| 3,690,312 | 9/1972 | Leibensohn | 128/674 |
| 3,730,168 | 5/1973 | McWhorter | 128/674 |
| 3,788,132 | 1/1974 | Trimble et al. | 116/DIG. 47 |
| 3,807,389 | 4/1974 | Miller et al. | 128/2.05 |
| 4,282,881 | 8/1981 | Todd et al. | 128/674 |
| 4,466,804 | 8/1984 | Hino | 604/4 |
| 4,923,442 | 5/1990 | Segall et al. | 128/898 |
| 5,088,771 | 2/1992 | Hosseinian et al. | 285/417 |
| 5,163,913 | 11/1992 | Rantanen-Lee et al. | 604/177 |

OTHER PUBLICATIONS

Greenwood, Assessment of Arteriovenous Fistulae from Pressure and Thermal Dilution Studies, Clinical Nephrology, 1985, vol. 23, pp. 189–197.

Gani, Use of the Fistula Assessment Monitor to Detect Stenoses in Access Fistulae, American Jour. of Kidney Diseases, 1991, vol. 18, pp. 303–306.

Schwab, Prevention of Hemodiaysis Fistula Thrombosis, Early Detection of Venous Stenoses. Kidney International, 1989, vol. 36, pp. 707–711.

Dorrell, Dialysis Access Stenosis and Intra–Access Pressure, Journal of the American Society of Nephrology, 1991, vol. 2, p. 322.

*Primary Examiner*—Kyle L. Howell
*Assistant Examiner*—Robert L. Nasser, Jr.

[57] ABSTRACT

A method and devices for measuring pressure within blood vessels used for hemodialysis and also for flow of blood into or from such blood vessels during hemodialysis. In one aspect of the method, a currently available hemodialysis set is used. This set comprises a tube (14) attached at one end to a hollow needle (12) and closed at the other end by a cap (19) which covers a proximal connector (18). The method comprises puncturing the blood vessel with the needle (12), measuring the distance to which blood flows under pressure into tube (14), calculating that pressure from that distance, and finally using the hemodialysis set for flow of blood in the performance of hemodialysis. In other aspects of the method, the improved devices of the invention are used. In one embodiment a proximal portion comprising a hollow needle (12), tube (14) with calibrated markings (16) and a proximal connector (18) are attached to a distal portion comprising a male connector (32) with lumen occluded by a hollow needle with a capillary lumen (34) and closed cylinder (24). The improvements in this embodiment increase the length of tube filled by blood and decrease the fluctuation in that length as a result of change in pressure between systole and diastole. In another embodiment a one-way flap valve (50) allows measurement of the maximum or systolic pressure within the blood vessel. In other embodiments pressure measurements are normalized for different atmospheric pressures at different altitudes. After the measurement of pressure, the needle, tube, and proximal connector are used for withdrawal or return of blood for a hemodialysis treatment.

9 Claims, 4 Drawing Sheets

FIG. 1
PRIOR ART
FIG. 2
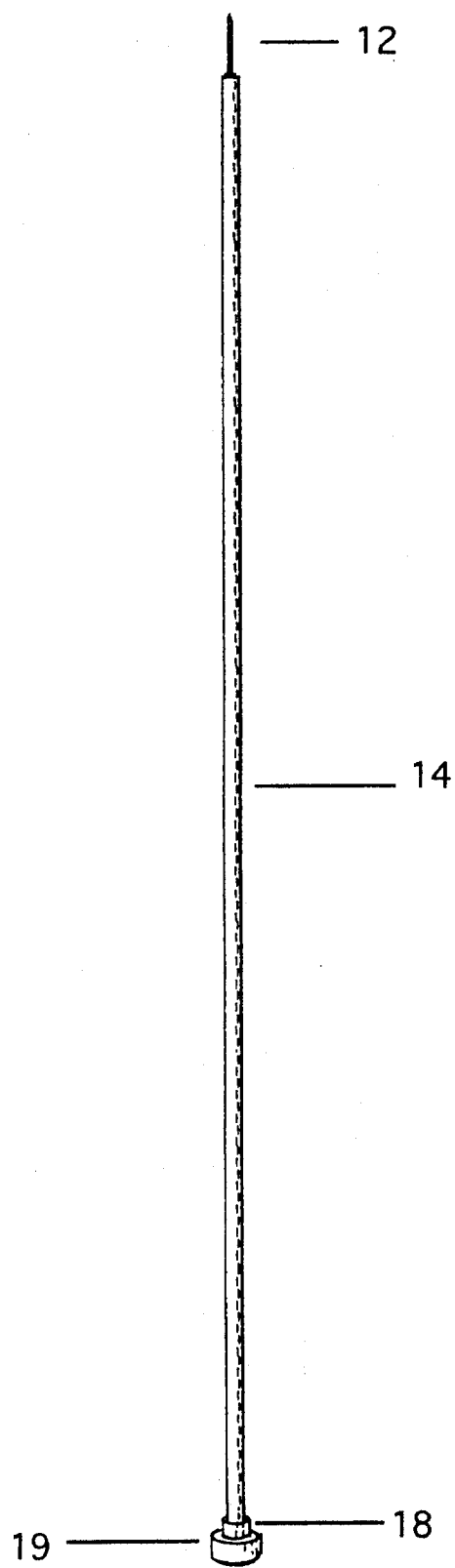
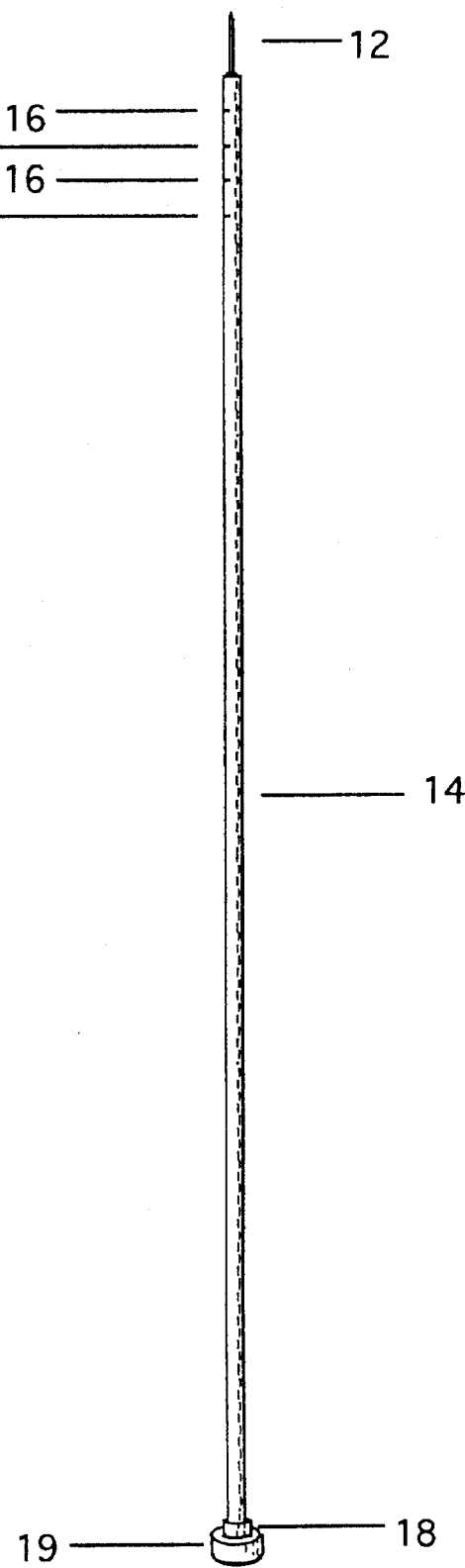

PRESSURE-MEASURING METHOD AND NEEDLE SYSTEM FOR HEMODIALYSIS

BACKGROUND—FIELD OF INVENTION

This invention relates to methods and devices for measuring pressure in blood vessels using a liquid column, specifically to a method for measuring pressure within blood vessels within blood vessels used for hemodialysis and an improved needle and tube system serviceable both for the measurement of pressure within such blood vessels and also for drawing or returning blood at the high rates of flow necessary for hemodialysis.

BACKGROUND—DESCRIPTION OF PRIOR ART

Over 100,000 patients in the United States depend on long-term hemodialysis, or artificial kidney treatments, to live. Access to blood for hemodialysis is provided by two types of blood vessels, hereinafter referred to simply as blood vessels. The first type is a vein which has been surgically connected to an artery. The second type is a synthetic blood vessel placed beneath the skin and connecting an artery and a vein. The most common cause of failure of these blood vessels is clotting. The most common cause of this clotting is the development of narrowing either at the connection of the blood vessel with the patient's vein or within the vein itself, hereinafter referred to as venous stenosis. If the venous stenosis is detected prior to clotting, it can be corrected far more easily than if the blood vessel has already clotted. Venous stenosis, by impeding flow of blood out of the blood vessel, causes an increase in pressure within the blood vessel. Consequently, measurement of this pressure allows early detection and correction of these stenoses.

Heretofore, techniques for accurately measuring pressure within hemodialysis blood vessels have required specialized training and electronic devices. These methods are too costly and difficult to use routinely in screening large numbers of patients. Greenwood and Gani have reported that venous stenosis is indicated by an average pressure within the blood vessel of over 60 millimeters of mercury. Dorrell has reported that venous stenosis is indicated by an average pressure within the blood vessel greater than forty percent of the average arterial pressure taken by blood pressure cuff.

Schwab has described a method in which pressure is measured within the tube of the dialysis machine which is returning blood into the patient's blood vessel. This uses the electronic pressure transducer already incorporated into the hemodialysis machine and does not require additional equipment. However, this method is inaccurate in measuring pressure within the patient's blood vessel. There is a difference in pressure between the tube within the machine and the patient's blood vessel. This difference varies with blood flow rate, blood viscosity, size of the needle puncturing the blood vessel and hydrostatic pressure generated by the fluid column between the tube in the machine and the patient's blood vessel.

Heretofore, inexpensive devices for measurement of fluid pressure within the human body have used liquid columns. They have required either the determination of the height of a manometric column of aqueous fluid or the determination of the distance to which fluid flows into a tube attached to a closed air space. The former method has long been used for measurement of pressures in veins. It is inconvenient for the high pressures within blood vessels used for hemodialysis. A pressure of 60 millimeters of mercury is equivalent to a column of aqueous fluid 812 millimeters high.

The latter method is used in three articles of prior art.

The capillary dimension of the tube in the Body Fluid Measure Device in U.S. Pat. No. 3,062,202 to Hyman and Winsor, 1962, Nov. 6, does not allow the same device to be used also for withdrawal or return of blood at the high flow rates required for hemodialysis treatments. Moreover, the tube and needle cannot be disconnected from the air reservoir after the measurement of pressure.

The Medical Instrument for Measuring Fluid Pressure in U.S. Pat. No. 3,807,389 to Miller, Sturman and Kanbar, 1974, Apr. 30, has a through passage for administration of fluid but requires a valve chamber, vent and valve member which increase cost and complexity.

Manometer for Infusion Apparatus, U.S. Pat. No. 4,282,881 to Todd, Smith and Reynolds, 1981, Aug. 11, is a manometer for measuring the hydrodynamic pressure of fluids parenterally administered to a patient. It comprises a housing having a fluid inlet and a fluid outlet, a through passageway in the housing accomodating continuous flow of fluid, a pressure measuring chamber in communication with the passageway at one end and with a closed air space at the other end, and reference markings associated with the pressure measuring chamber for measuring the pressure of fluid flowing through the passageway. Unlike the current invention, the pressure measuring chamber branches off from the through passageway in a dead end and is not removable. If this manometer were used for hemodialysis rather than fluid administration, the stagnant blood within the pressure measuring chamber would clot. Fragments of clot could then pass into the through passageway and into the patient during the subsequent hemodialysis. Moreover, the pressure measuring chamber and air space remain attached to the through passageway. Thus a bulky, rigid apparatus would remain attached to the patient during the hemodialysis.

Moreover, none of the above prior art, which are designed for measurement of pressures within veins, provides a way to dampen oscillation of the fluid column. Pressure within hemodialysis blood vessels can double with each heartbeat between its maximum or systolic pressure and its minimum or diastolic pressure. Dampening this oscillation is desirable to determine more easily the average fluid pressure in blood vessels used for hemodialysis. Finally, none of the above methods allows determination of the maximum fluid pressure. Because of resistance to flow and inertia of the fluid column, the maximum oscillation of the fluid column in the above methods does not correspond to the true maximum or systolic pressure within the blood vessel.

In one aspect, the method of this invention can use a hemodialysis set produced by a number of manufacturers. This set is comprised of a needle, tube, connector and cap. It is routinely used now for withdrawing or returning blood in the performance of hemodialysis. This hemodialysis set is not a departure from prior art. However, a method using this hemodialysis set for the measurement of pressure within the blood vessels used for hemodialysis has never been reported in prior art.

In another aspect, my invention relates to improved devices using this same method, which is applicable both to currently available hemodialysis sets and to the improved devices I have invented.

Accordingly, prior art has reported no simple, inexpensive yet accurate method or device usable both for measuring the pressure within hemodialysis blood vessels and for the performance of hemodialysis.

SUMMARY OF INVENTION

The method of this invention comprises a new use for the standard hemodialysis needle, tube, connector, and cap wherein, after the blood vessel is punctured by the needle, the distance to which blood is pushed back into the tube is measured and from this distance the pressure in the blood vessel is ascertained. Following this new use, the needle, tube, connector, and cap are used routinely for withdrawal or return of blood in performance of hemodialysis. The method of this invention can also use the improved devices of this invention. One such device comprises an improvement upon the standard needle, tube, connector and cap wherein calibrated markings are placed on the tube to allow pressure to be ascertained directly from the markings. A further improvement comprises an air reservoir attached to the tube which increases the distance to which blood flows into the tube. Further improvements comprise modifications which allow better measurement of average or peak (systolic) pressure and allow calibration for different altitudes.

OBJECTS AND ADVANTAGES

It is the object of this invention to provide a simple, reliable method and an inexpensive, disposable medical device which will allow a technician with minimal training quickly, easily, and accurately to determine the fluid pressure within a blood vessel used for hemodialysis and also to use the same device for withdrawal or return of blood for the hemodialysis treatment.

The advantages of this invention are as follows:

1. The simplicity of this method is easily understandable and is inherently reliable because it relies on a simple physical law of gaseous compression and does not require calibration.

2. In it's simplest form this method can be performed using equipment already easily available without additional cost.

3. The simplicity of design allows production of even the more improved embodiments at a very low cost, hence a new sterile device could be used for each pressure measurement, thereby avoiding the risk of bacterial or vital contamination when devices are used repeatedly.

4. The dual function both for pressure measurement and for the subsequent hemodialysis treatment further reduces the incremental cost above the hemodialysis treatment alone and spares the patient the pain having his blood vessel punctured an additional time.

5. The removal of the air space in the improved embodiments after the pressure measurement leaves the patient attached to only the usual needle and tube routinely used for the hemodialysis treatment.

6. The simplification over prior pressure measuring devices of not having a separate through-channel and pressure-measuring channel avoids the formation of clot within the stagnant pressure-measuring channel.

7. The dampening of oscillation in the fluid column in two embodiments allows easier and more accurate determination of average pressure or of maximum pressure within the hemodialysis blood vessel.

8. Since pressure measurements can be made easily, quickly, inexpensively, and without additional discomfort to the patient, they can be performed frequently. This will allow prompt detection of changes in a patient's blood vessel by comparing the current pressure with previous measurements in the same patient. Since this is an entirely new capability, there is no reported experience with this frequent monitoring of pressure, but it is a reasonable expectation that this frequent monitoring will be a major medical advance in saving these hemodialysis blood vessels and hence in saving patient's lives.

DESCRIPTION OF DRAWINGS

FIG. 1 is a perspective view of the hemodialysis set which is already widely used for withdrawing or returning blood in the performance of hemodialysis and which is used for a new purpose in the method of this invention.

FIG. 2 is a perspective view of the first embodiment of the device of this invention.

REFERENCE NUMERALS IN DRAWINGS

Figure 3:
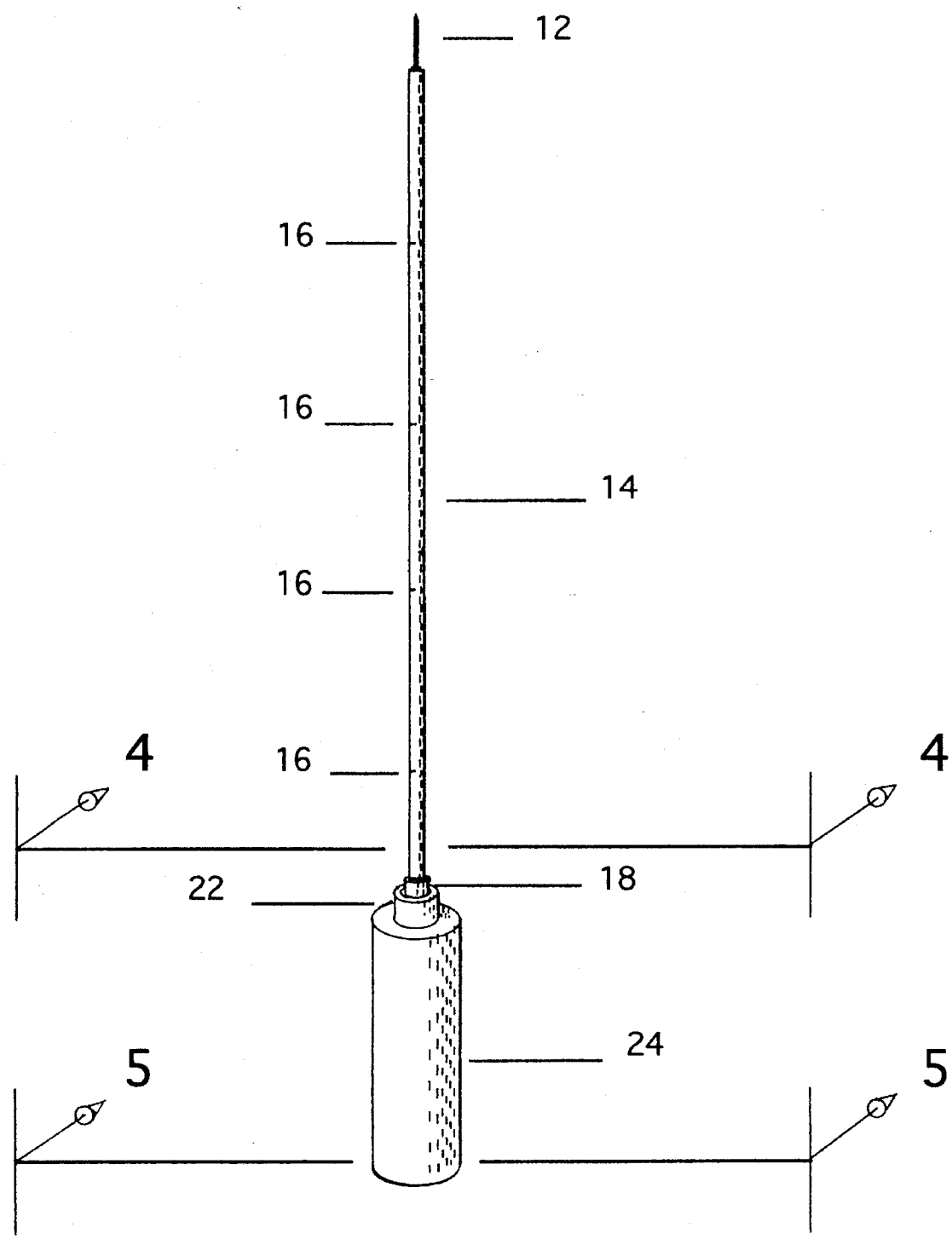
FIG. 3 is a perspective view of the second embodiment of the invention.

12—hollow needle
14—transparent tube
16—set of calibrated markings
18—proximal connector
19—cap
20—male connector
22—outer barrel with spiral thread on inner surface
24—closed cylinder
26—pair of anchoring wings
28—second set of calibrated markings normalized for a different altitude
32—male connector with occluded lumen
34—hollow needle with capillary lumen
36—closed cylinder with threaded hole
38—plunger
40—bolt with spiral thread
42—set of markings calibrated for different altitudes
44—reference strip
46—set of columns of calibrated markings indicating pressure at different altitudes
48—set of altitudes for each column of calibrated markings
50—one-way flap valve

DESCRIPTION—FIG. 1—METHOD INVENTED

FIG. 1 shows a perspective view of the equipment used in the method of this invention in its simplest aspect. This equipment is commercially available and is not a new device. A hollow needle 12 is formed from extruded metal tube and cut with a sharp angled bevel on one end and a transverse cut on the other end. A transparent tube 14 is connected to needle 12. Tube 14 is manufactured by continuous extrusion and cut to appropriate length. Any material which is not antagonistic to human blood, transparent and not overly distensible can be used. Suitable plastics are polypropylene and polyvinylchloride. A proximal connector 18 is attached to the end of the tube opposite needle 12. A cap 19 contains a Luer fitting, which incorporates a spiral thread on the inner surface of the cap. Any material which is impermeable to air can be used for the cap. One suitable plastic is polystyrene.

DESCRIPTION—FIG. 2—FIRST EMBODIMENT

FIG. 2 shows a perspective view of the first embodiment of the device of this invention. A plurality of calibrated markings 16 are impressed, applied, engraved or the like on tube 14 at positions corresponding to different pressures within the vessel punctured by needle 12. Markings 16 for different pressures are differentiated by color or by an adjacent number. Markings 16 are calibrated for different altitudes such as sea level, 3000 feet and 6000 feet on different versions supplied to users at different altitudes. A compensation of only 9.6% for every 3000 feet of altitude will suffice to correct.

Figure 4:
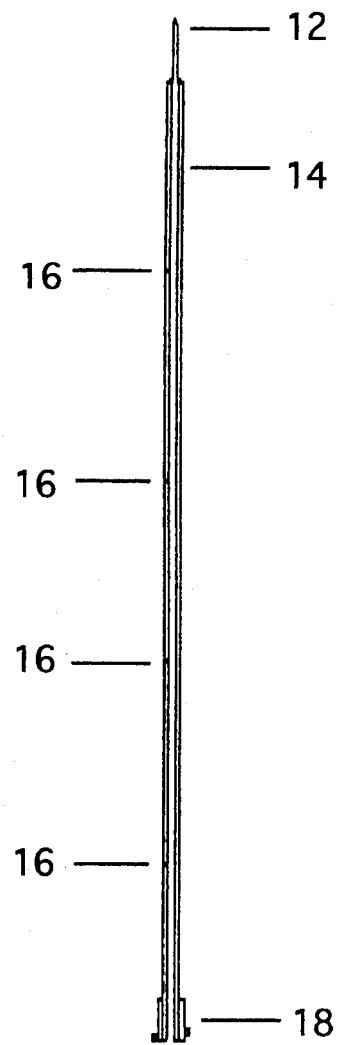
FIG. 4 is an axial cross section of the proximal portion of the second embodiment in FIG. 3 taken along lines 2—2.
Figure 5:
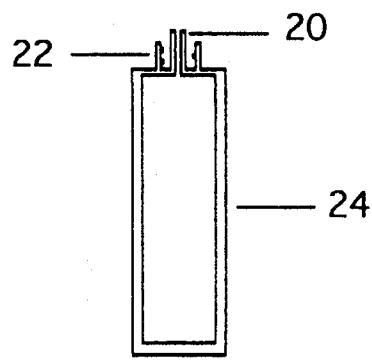
FIG. 5 is an axial cross-section of the distal portion of the second embodiment in FIG. 3 also taken along lines 2—2.

DESCRIPTION—FIGS. 3, 4 and 5—SECOND EMBODIMENT

Needle 12, tube 14, reference markings 16 and proximal connector 18 comprise the proximal portion of the invention. This is removed from the distal portion after pressure measurement. It is used during the hemodialysis treatment for the withdrawal or return of blood.

The proximal portion of the invention is connected at proximal connector 18 to the distal portion with a male connector 20, not visible in this perspective view. Male connector 20 is surrounded by a Luer fitting, which incorporates a spiral thread on the inner surface of outer barrel 22, which is attached to a closed cylinder 24. Any rigid extrudible material which is impermeable to air can be used for the distal portion of invention. One suitable plastic is polystyrene.

FIG. 4 is an axial cross section of the proximal portion of the second embodiment in FIG. 1 taken along lines 2—2. A continuous lumen is shown passing through needle 12, tube 14, and proximal connector 18.

FIG. 5 is an axial cross section of the distal portion of the second embodiment in FIG. 1 also taken along lines 2—2. When proximal connector 18 is screwed into the spiral thread on the inner surface of outer barrel 22, proximal connector 18 forms an air-tight seal with male connector 20. Male connector 20 is attached to closed cylinder 24. When proximal portion in FIG. 4 is attached to distal portion in FIG. 5, a continuous lumen passes from needle 12 to cylinder 24.

DESCRIPTION—FIGS. 6 AND 7—THIRD EMBODIMENT

Figure 6:
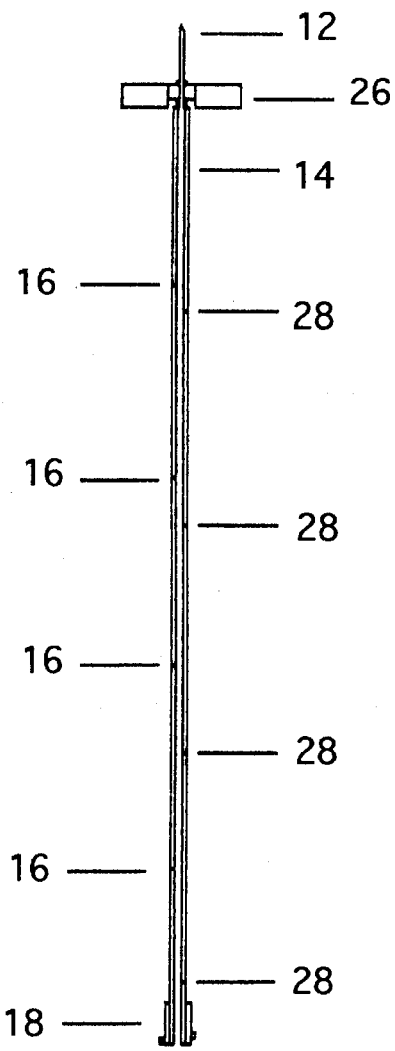
FIG. 6 is an axial cross-section of the proximal portion of the third embodiment of the invention.

FIG. 6 is an axial cross section view of the proximal portion of a third embodiment of the invention taken along the same line as FIG. 4. A pair of anchoring wings 26 made of plastic or any other material to which tape will adhere are inserted between needle 12 and tube 14. In addition to markings 16 calibrated for one altitude, a second set of markings 28 calibrated for a second altitude is impressed, applied, engraved or the like onto tube 14.

Figure 7:
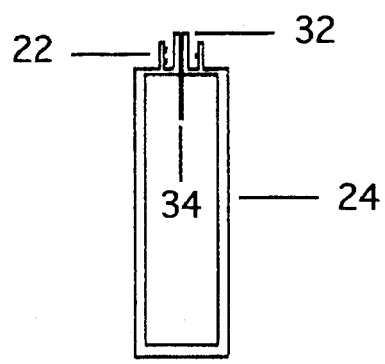
FIG. 7 is an axial cross section of the distal portion of the third embodiment of the invention.

FIG. 7 is an axial cross-section view of the distal portion of the third embodiment of the invention taken along the same line as FIG. 5. A male connector with an occluded lumen 32 replaces male connector with large lumen 20 shown in FIG. 5. A hollow needle 34 contains a lumen of capillary dimensions and extends through male connector with occluded lumen 32 into the cavity of cylinder 24. This long capillary lumen increases the resistance to flow of air between the proximal and distal portions of the invention.

DESCRIPTION—FIGS. 8 AND 9—FOURTH EMBODIMENT

Figure 8:
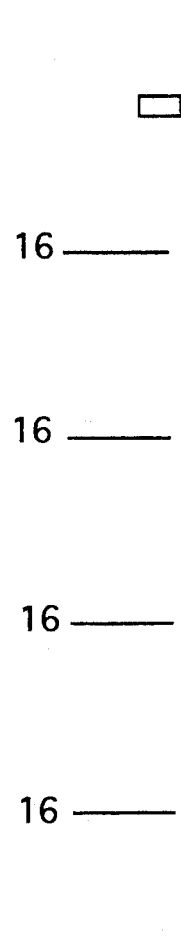
FIG. 8 is an axial cross section of the proximal portion of the fourth embodiment of the invention.

FIG. 8 is an axial cross section view of the proximal portion of the fourth embodiment of the invention taken along the same line as FIGS. 4 and 6. Needle 12, anchoring wings 26, tube 14, reference markings 16, and proximal connector 18 are identical to the proximal portion of the third embodiment shown in FIG. 6. Only second set of reference markings 28 is omitted.

Figure 9:
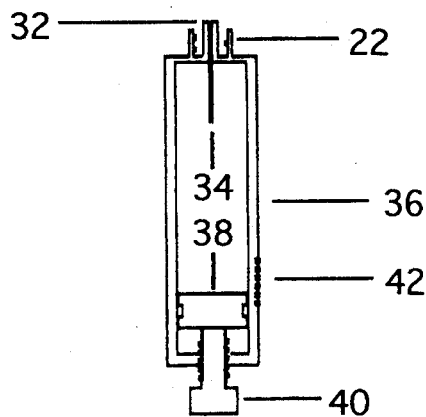
FIG. 9 is an axial cross section of the distal portion of the fourth embodiment of the invention.

FIG. 9 is an axial cross-section view of the distal portion of the fourth embodiment of the invention taken along the same line as FIGS. 5 and 7. Male connector with occluded lumen 32, outer barrel with spiral thread 22 and hollow needle with capillary lumen 34 are identical to the embodiment shown in FIG. 7. Male connector 32 is attached to a cylinder 36, which differs from cylinder 24 in previous embodiments in having a spirally threaded hole at the end opposite male connector 32. A spirally threaded bolt 40, passing through the threaded hole, is attached to and moves a plunger 38. Plunger 38 forms an air-tight seal with the sides of cylinder 36. A set of markings 42 are impressed, applied, engraved or the like on cylinder 36, which is transparent in this embodiment. Markings 42 are calibrated so that when the plunger is moved adjacent to the appropriate marking the invention is normalized for a particular altitude.

DESCRIPTION—FIGS. 10 AND 11—FIFTH EMBODIMENT

Figure 10:
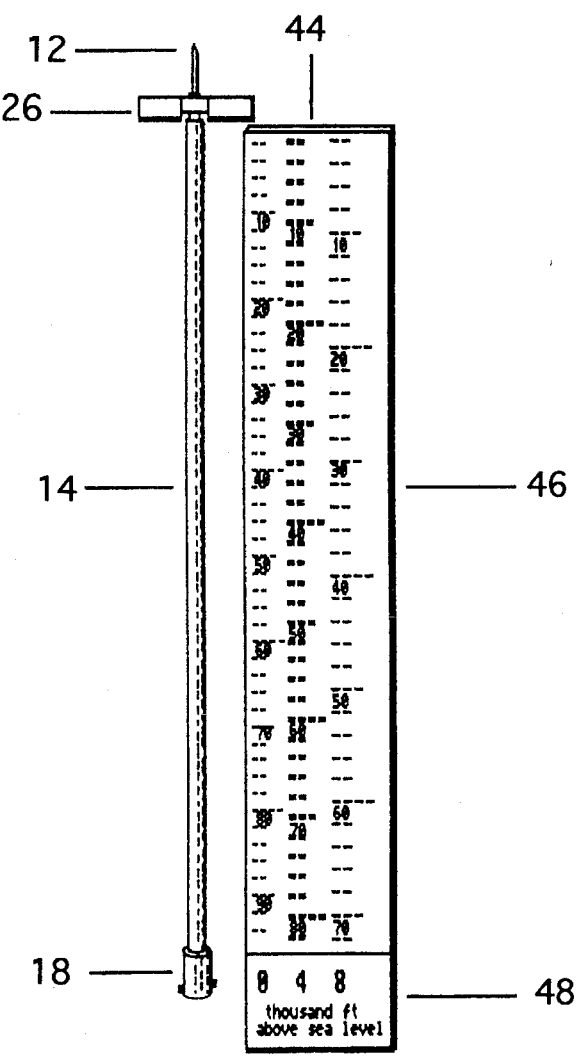
FIG. 10 is a perspective view of the proximal portion of the fifth embodiment of the invention.

FIG. 10 is a perspective view of the proximal portion of the fifth embodiment of the invention. Needle 12, anchoring wings 26, tube 14, and proximal connector 18 are identical to the proximal portion of the third embodiment shown in FIG. 6. Markings 16 and second set of markings 28 are not applied to tube 14, but instead a reference strip 44 is separately supplied. A set of columns of calibrated markings 46 indicating pressures at different altitudes and a set of altitude labels 48 with one label for each column of calibrated markings 46 are impressed, applied, engraved or the like on reference strip 44.

Figure 11:
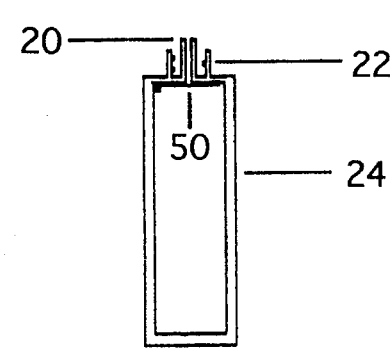
FIG. 11 is an axial cross section of the distal portion of the fifth embodiment of the invention.

FIG. 11 is an axial cross-section view of the distal portion of the fifth embodiment of the invention taken along the same line as FIGS. 5, 7 and 9. Male connector 20 is covered by a one-way flap valve 50. Flap valve 50 is comprised of a thin disk of flexible material which is impermeable to air and which is attached around most of its circumference to the end of cylinder 24. When air flows from tube 14 into cylinder 24, valve 50 is pushed away from the lumen of male connector 20. When air begins to flow from cylinder 24 into tube 14, valve 50 occludes the lumen of male connector 20.

OPERATION—METHOD INVENTED

The hemodialysis set shown in FIG. 1 is used in the simplest version of the method invented. Cap 19 is attached to proximal connector 18, making tube 16 a closed system. Needle 12 is placed into the patient's blood vessel. Tube 16 is secured with tape to the patient's skin. The pressure within the blood vessels causes a column of blood to enter tube 16.

According to Boyle's Law, the volume occupied by the air within tube 14 after entry of the blood into the tube will equal the initial volume within the tube multiplied by the ratio of the air pressure after entry of the blood divided by the initial atmospheric pressure. It can be demonstrated that the length of tube 14 occupied by blood $L_b = V/A * P_b/(P_a + P_b)$, where V is the initial volume of air contained in tube 14, A is the cross-sectional area of tube 14, $P_b$ is the pressure within the blood vessel, and $P_a$ is the atmospheric pressure. $P_a$ is normally 760 millimeters of mercury with a variation of about 2.5% at sea level. $P_a$ decreases about 3.2% with each 1000 feet increase in altitude. In the simplest version of this method, V equals total length of tube 14, $L_t$, multiplied by A. Therefore, $L_b = L_t * P_b/(P_a + P_b)$. Finally, $P_b = P_a * L_b/(L_t - L_b)$. Thus, for any given length of tube 14 ($L_t$) and atmospheric pressure ($P_a$), pressure within the blood vessel ($P_b$) can be computed from the length of tube 14 occupied by blood ($L_b$). The relationship between $P_b$ and $L_b$ can also be determined empirically, a table or scale can be determined, and for any $L_b$ the $P_b$ can be determined from that table or scale.

The length of tube 14 occupied by blood will vary between a maximum and a minimum length determined largely by the maximum or systolic pressure and the minimum or diastolic pressure within the blood vessel. The variation will be accentuated somewhat by the momentum of the blood moving within tube 14. It will be decreased somewhat by the viscous resistance to flow within needle 12. Therefore, the position of the interface or meniscus between blood and air within tube 14 relative to calibrated markings 16 will yield an approximation of the systolic and diastolic pressures within the blood vessel.

The above method which has now been invented is an entirely new and previously unreported use of the hemodialysis set in FIG. 1. After this method is used the equipment then can be used for its routine purpose. A clamp is applied to tube 14, cap 19 is removed from proximal connector 18, and the equipment is used for the withdrawal or return of blood for hemodialysis. Hereinafter, the withdrawal of the blood from the patient's blood vessel into the hemodialysis machine and the return of blood from the hemodialysis machine into the patient's blood vessel will be referred to as the flow of blood. This flow of blood is customarily at a rate greater than 150 milliliters per minute. This rate is necessary for sufficient hemodialysis to be performed within a reasonable amount of time, usually less than four hours.

OPERATION—FIRST EMBODIMENT

The first embodiment shown in FIG. 2 is an improved device with which the pressure within the blood vessel is ascertained by noting the position of the meniscus between, blood and air within tube 14 relative to the calibrated markings 16.

OPERATION—SECOND EMBODIMENT

The second embodiment is distributed in a sealed, sterilized package with the proximal portion shown in FIG. 4 and distal portion shown in FIG. 5 connected. When needle 12 has entered the blood vessel, the pressure of blood within the blood vessel will force blood through needle 12 and into tube 14, compressing the air within tube 14 and cylinder 24 until the air pressure equals the fluid pressure within the blood vessel. Since $L_b = V/A * P_b/(P_a + P_b)$, the increase in V caused by the air reservoir within cylinder 24 results in a magnification in $L_b$. Therefore, calibrated markings 16 are more widely spaced allowing more accurate ascertainment of the pressures within the blood vessel.

After pressure measurement, tube 14 is occluded by any commercially available clamp. Male connector 20 and the remainder of the distal portion shown in FIG. 3 are removed. Only the proximal portion shown in FIG. 2 is left attached to the patient and is used for return of blood or for withdrawal of blood during the hemodialysis treatment.

OPERATION—THIRD EMBODIMENT

FIGS. 6 and 7 show the second embodiment, which is presently preferred. The proximal and distal portions are connected at male connector 32 and proximal connector 18. Needle 12 is placed in the patient's blood vessel. Pair of anchoring wings 26 are taped to the patient's skin and provide a larger surface for taping. Blood flows into tube 14 and thus air pressure in tube 14 increases. Because of the resistance inherent in the capillary lumen in hollow needle 34, air flows slowly into cylinder 24. Air pressure in cylinder 24 will fluctuate much less than in the first embodiment and will approximate the average pressure in the hemodialysis blood vessel. Only the much smaller volume of air remaining within tube 14 fluctuates in pressure as the pressure in the blood vessel fluctuates between cardiac systole and diastole. Therefore, the volume in total of air within cylinder 24 and tube 14 and also the volume of blood within tube 14 will fluctuate less between cardiac systole and diastole. The average fluid pressure within the blood vessel is read from the average location of the meniscus between the blood and air relative to set of calibrated markings 16 or second set of calibrated markings normalized for a different altitude 28. Tube 14 is clamped. Finally, the distal portion of the second embodiment shown in FIG. 7 is removed and the proximal portion shown in FIG. 6 is used for the hemodialysis treatment as described for the first embodiment.

OPERATION—FOURTH EMBODIMENT

The fourth embodiment is shown in FIG. 8, the proximal portion, and FIG. 9, the distal portion. These are connected as in previous embodiments. Bolt with spiral thread 40 is turned, moving plunger 36 to an appropriate position relative to markings calibrated for different altitudes 42. Atmospheric pressure $P_a$ is much greater than the blood vessel pressure $P_b$. Therefore, decreasing the volume V contained within tube 14 and cylinder 36 in proportion to any decrease in atmospheric pressure $P_b$ will keep $V/(P_a + P_b)$ approximately constant. The length of tube 14 occupied by blood equals $V/A * P_b/(P_a + P_b)$ as above and will thus remain proportional to $P_b$. The remainder of the operation follows the description for the second embodiment.

OPERATION—FIFTH EMBODIMENT.

The fifth embodiment is shown in FIGS. 10 and 11. Again, the proximal and distal portions are connected, needle 12 is inserted into the blood vessel, and anchoring wings 26 are taped to the patient. Reference strip 44 is placed beneath tube 14 and the position of the meniscus between blood and air is read relative to pressure markings 46 in the column marked for the appropriate altitude 48. Since one-way flap valve 50 allows flow of air only from tube 14 into cylinder 24, air pressure within cylinder 24 will approximate the maximum or systolic blood pressure within the hemodialysis blood vessel. Thus the pressure reading from the meniscus will approximate that systolic pressure within the blood vessel.

SUMMARY, RAMIFICATIONS, AND SCOPE

Accordingly, the reader will see that the pressure-measuring method and needle system for hemodialysis of this invention makes possible for the first time the simple, accurate, rapid, convenient and inexpensive measurement of pressure within hemodialysis blood vessels. The different embodiments allow measurement of systolic, diastolic, and mean pressure and allow the system to be used at any altitude. Moreover, this measurement is important to maintenance of these blood vessels and thus important to the welfare of tens of thousands of patients.

While my above description contains many specificities, these should not be construed as limitations on the scope of the invention, but rather as exemplifications thereof with five embodiments. Many other variations are possible. Anchoring wings 26 can have many shapes or may be single. The lumen of male connector 32 may be occluded with semi-porous material instead of hollow needle 34 in order to increase resistance to air flow. Cylinders 24 and 36 may be modified into other shapes, such as cubical or spherical. The proximal portions in FIGS. 4, 6, 8 and 10 can be connected to the distal portions in FIGS. 5, 7 and 11 in any combination.

Accordingly, the scope of the invention should be determined not by the embodiments illustrated, but by the appended claims and their legal equivalents.

I claim:

1. A medical device for measuring pressure within blood vessels used for hemodialysis and also for withdrawing or returning blood in the performance of hemodialysis, comprising:
   (a) means for puncturing said vessels located at a proximal end of said medical device;
   (b) a tube attached to said puncturing means;
   (c) blood pressure measuring means, associated with said tube, comprising reference means for measuring a distance to which a column of blood has entered said tube, said reference means comprising a plurality of calibrated markings placed upon said tube at positions corresponding to different pressures within said blood vessels, said plurality of calibrated markings being distinguishable in a plurality of sets each corresponding to a different altitude at which said medical device is used;
   (d) a first connector attached to a distal end of said tube;
   (e) a second connector forming with said first connector an air-tight connection;
   (f) a closed chamber, attached to said second connector, that defines a non-expansible volume.

2. A blood pressure measuring kit for measuring pressure within blood vessels used for hemodialysis and also for withdrawing or returning blood in the performance of hemodialysis, comprising:
   (a) means for puncturing said vessels
   (b) a tube attached to said puncturing means;
   (c) a first connector attached to a distal end of said tube;
   (d) a second connector forming with said first connector an air-tight connection;
   (e) a closed chamber, attached to said second connector, that defines a non-expansible volume;
   (f) blood pressure measuring means, associated with but not attached to said tube, comprising reference means for measuring a distance to which a column of blood has entered said tube, said reference means comprising an essentially flat strip of material placed adjacent said tube, said strip having a plurality of calibrated markings placed at positions corresponding to different pressures within said blood vessels, said plurality of calibrated markings being distinguishable in a plurality of sets each corresponding to a different altitude at which said blood pressure measuring kit is used.

3. A medical device for measuring pressure within blood vessels used for hemodialysis and also for withdrawing or returning blood in the performance of hemodialysis, comprising:
   (a) means for puncturing said vessels located at a proximal end of said medical device;
   (b) a tube attached to said puncturing means;
   (c) blood pressure measuring means, associated with said tube, comprising reference means for measuring a distance to which a column of blood has entered said tube;
   (d) a first connector attached to a distal end of said tube;
   (e) a second connector forming with said first connector an air-tight connection;
   (f) a closed chamber, attached to said second connector, that defines a non-expansible volume;
   (g) means for producing greater resistance to flow of air between said tube and said closed chamber than the resistance to flow of air within said tube.

4. The medical device of claim 3 wherein said means for producing greater resistance to flow of air between said tube and said closed chamber than the resistance to flow of air within said tube comprises a capillary lumen within said second connector.

5. The medical device of claim 3 wherein said second connector contains a lumen and wherein said means for producing greater resistance to flow of air between said tube and said closed chamber than the resistance to flow of air within said tube comprises a porous material filling said lumen.

6. A blood pressure measuring kit for measuring pressure within blood vessels used for hemodialysis and also for withdrawing or returning blood in the performance of hemodialysis, comprising:
   (a) means for puncturing said vessels;
   (b) a tube attached to said puncturing means;
   (c) a first connector attached to a distal end of said tube;
   (d) a second connector forming with said first connector an air-tight connection;
   (e) a closed chamber, attached to said second connector, that defines a non-expansible volume;
   (f) means for producing greater resistance to flow of air between said tube and said closed chamber than the resistance to flow of air within said tube;
   (g) blood pressure measuring means, associated with but not attached to said tube, comprising reference means for measuring a distance to which a column of blood has entered said tube, said reference means comprising an essentially flat strip of material placed adjacent said tube, said strip having a plurality of calibrated markings placed at positions corresponding to different pressures within said blood vessels.

7. A medical device for measuring pressure within blood vessels used for hemodialysis and also for withdrawing or returning blood in the performance of hemodialysis, comprising:
   (a) means for puncturing said vessels located at a proximal end of said medical device;
   (b) a tube attached to said puncturing means;
   (c) blood pressure measuring means, associated with said tube, comprising reference means for measuring a distance to which a column of blood has entered said tube;
   (d) a first connector attached to a distal end of said tube;
   (e) a second connector forming with said first connector an air-tight connection;
   (f) a closed chamber, attached to said second connector, that defines a non-expansible volume;
   (g) means for allowing flow of air only in one direction from said tube into said closed chamber and for preventing flow of air from said closed chamber into said tube.

8. The medical device of claim 7 wherein said second connector contains a lumen, wherein said closed chamber has a base, wherein said lumen has an opening into said base of said closed chamber and wherein said means for allowing flow of air only in one direction from said tube into said closed chamber and for preventing flow of air from said closed chamber into said tube comprises a thin, flexible disk which is impermeable to air, is attached around a portion of its circumference to said base of said closed chamber, and overlies said opening of said lumen of said second connector into said closed chamber.

9. A blood pressure measuring kit for measuring pressure within blood vessels used for hemodialysis and also for withdrawing or returning blood in the performance of hemodialysis, comprising:
   (a) means for puncturing said vessels;
   (b) a tube attached to said puncturing means;
   (c) a first connector attached to a distal end of said tube;
   (d) a second connector forming with said first connector an air-tight connection;
   (e) a closed chamber, attached to said second connector, that defines a non-expansible volume;
   (f) means for allowing flow of air only in one direction from said tube into said closed chamber and for preventing flow of air from said closed chamber into said tube;
   (g) blood pressure measuring means, associated with but not attached to said tube, comprising reference means for measuring a distance to which a column of blood has entered said tube, said reference means comprising an essentially flat strip of material placed adjacent said tube, said strip having a plurality of calibrated markings placed at positions corresponding to different pressures within said blood vessels.

* * * * *